United States Patent [19]

Ball

[11] 4,067,230
[45] Jan. 10, 1978

[54] DUAL TURBINE IN-LINE VISCOMETER AND FLOWMETER

[76] Inventor: John M. Ball, 3128 Millbrook Drive NW., Huntsville, Ala. 35810

[21] Appl. No.: 750,928

[22] Filed: Dec. 15, 1976

[51] Int. Cl.$^2$ ............................................. G01N 11/14
[52] U.S. Cl. ........................................ 73/54; 73/231 R
[58] Field of Search ............... 73/54, 231 R, 229, 195, 73/196

[56] References Cited

U.S. PATENT DOCUMENTS 3,710,622   1/1973   Hammond et al. ................. 73/231 R

FOREIGN PATENT DOCUMENTS 1,266,994   4/1963   Germany ............................. 73/229
1,804,439  10/1968   Germany ............................. 73/229

Primary Examiner—Richard C. Queisser
Assistant Examiner—Joseph W. Roskos
Attorney, Agent, or Firm—Nathan Edelberg; Robert P. Gibson; Charles R. Carter

[57] ABSTRACT

A viscometer for use in making viscosity measurements under operating conditions. The viscometer includes a large turbine and a small turbine both operated by the in-line fluid flow. By operating the two turbines simultaneously a comparison of their output frequencies can be made to indicate the ratio point and the viscosity of the fluid flowing is determined from the ratio point.

1 Claim, 2 Drawing Figures

DUAL TURBINE IN-LINE VISCOMETER AND FLOWMETER

DEDICATORY CLAUSE

The invention described herein may be manufactured, used and licensed by or for the Government for governmental purposes without the payment to me of any royalties thereon.

BACKGROUND OF THE INVENTION

This invention relates to the field of viscosity measuring. Present in-line viscometers in use are either inaccurate, too cumbersome or limited in their range for many applications.

SUMMARY OF THE INVENTION

The present invention can be used to make fluid flow measurements under use conditions without having to remove a sample for a time consuming laboratory measurement. The fluid to be measured is passed through a large fluid operated turbine which is operating in its non-linear range of response to flow rate. After passing through the large turbine the fluid is directed through a smaller diameter pipe to a small turbine which operates in the linear response range. A comparsion of the ratio of the observed output frequency of the non-linear meter to the linear meter's output frequency gives the viscosity of the fluid flowing.

This invention may be better understood from the following detailed description taken in conjunction with the accompanying drawing.

DESCRIPTION OF THE PREFERRED EMBODIMENT

Figure 1:
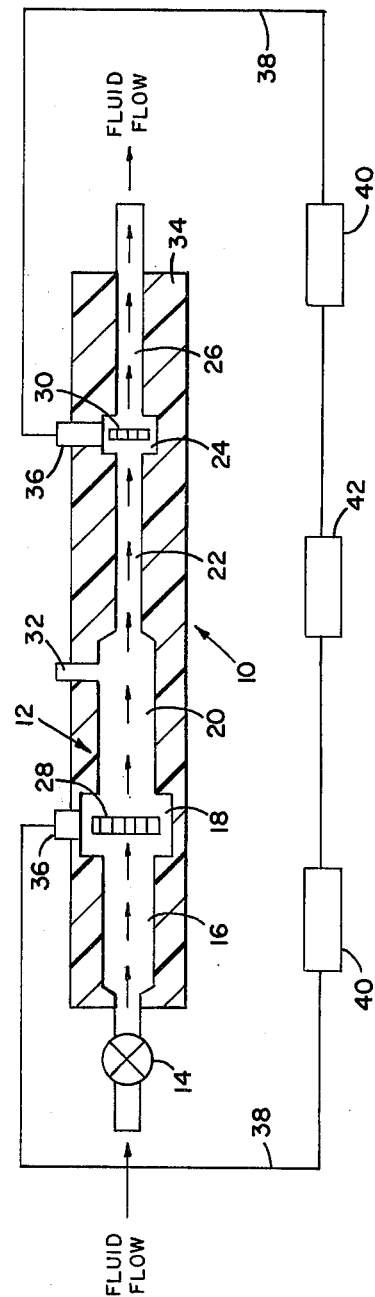
FIG. 1 is a schematic of the in-line viscometer at a measuring station.

As shown in FIG. 1 reference numeral 10 indicates an in-line viscometer at a viscosity measurement station. The viscometer includes a measuring unit 12 having its fluid flow inlet end controlled by a valve 14. The measuring unit consists of a large upstream flow straightner 16, a large diameter turbine housing 18, a large downstream flow straightner tube 20, a small upstream flow straightner 22, a small diameter turbine housing 24 and a small downstream flow straightner tube 26. A large fluid flow turbine 28 is located in housing 18 while a small fluid flow turbine 30 is located in housing 24. The large downstream tube 20 is provided with a temperature probe 32 and the entire unit 12 is encased by insulation 34 to insure an even temperature. Each of the housings 18 and 24 are provided with RF (modulated carrier) pickoffs 36 that are connected by signal lines 38 to frequency readouts 40 and to the frequency ratio indicator 42. The ratio indicator is a direct reading of the viscosity response of large turbine 28 to the viscosity response of small turbine 30.

Figure 2:
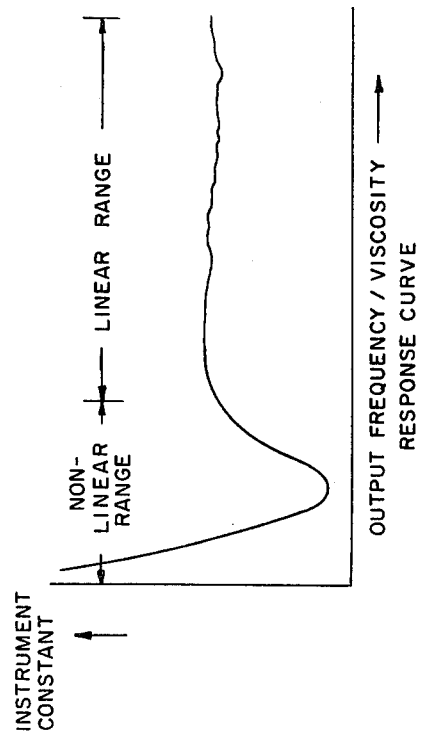
FIG. 2 is a graph of the response curve.

In operation, fluid is caused to flow through the viscosity measuring station by the opening of valve 14. The two turbines are of different sizes, in the order of $\frac{1}{2}$ to $\frac{3}{4}$, chosen so that when the smaller turbine is operating in its so-called "linear" range, the larger turbine is in its so-called "non-linear" range of response to the flow rate. Both of these ranges are shown on the response curve of FIG. 2. As can be observed from the response curve when a turbine meter is operating in its "linear range" it is fairly insensitive to the fluid viscosity. By operating the two turbines simultaneously the response frequency indicators 36 provide a frequency readout at 40 and a comparison of their output frequencies is indicated on the ratio indicator 40. One of the turbines will be operating in its "linear range" and the other turbine will be operating in the "non-linear range". Comparsion of the ratio point to the observed output frequency of the "non-linear" turbine will give the viscosity of the fluid flowing when compared wth a graph or table value.

I claim:

1. An apparatus for making fluid flow viscosity measurements during operating conditions comprising: a dual turbine in-line viscometer; said viscometer including an upstream flow straightner; a turbine housing; a turbine disposed in said housing; a downstream flow straightner; a second upstream flow straightner; a second turbine housing; a second turbine disposed in said second housing and a second downstream flow straightner; said second upstream flow straightner, second turbine housing, second turbine and second downstream flow straightner being of a smaller diameter than said first upstream flow straightner, turbine housing, turbine and downstream flow straightner; a frequency indicator connected to each of said housings; a frequency readout for reading each separate frequency and a frequency ratio indicator for comparing each of said frequency response; said in-line viscometer being provided with a temperature probe encased by insulation to control the temperature of said viscometer.

* * * * *